United States Patent
Wang et al.

US008142759B2

(10) Patent No.: US 8,142,759 B2
(45) Date of Patent: *Mar. 27, 2012

(54) GLYCO-MOLECULAR IMAGING METHOD FOR GRADE CLASSIFICATION OF LIVER FIBROSIS AND ITS GLYCO-MOLECULAR IMAGING AGENT THEREOF

(75) Inventors: Mei-Hui Wang, Taoyuan County (TW); Wuu-Jyh Lin, Taoyuan County (TW); Shui-Cheng Lee, Taoyuan County (TW); Lie-Hang Shen, Taoyuan County (TW); Haw-Jan Chen, Taoyuan County (TW)

(73) Assignee: Institute of Nuclear Energy Research, Jiaan Village, Longtan, Taoyuan (TW)

( * ) Notice: Subject to any disclaimer, the term of this patent is extended or adjusted under 35 U.S.C. 154(b) by 727 days.

This patent is subject to a terminal disclaimer.

(21) Appl. No.: 11/954,221

(22) Filed: Dec. 12, 2007

(65) Prior Publication Data

US 2009/0155169 A1    Jun. 18, 2009

(51) Int. Cl.
*A61K 51/00* (2006.01)
*A61M 36/14* (2006.01)

(52) U.S. Cl. .......... 424/1.69; 424/1.11; 424/1.65
(58) Field of Classification Search .......... 424/1.11, 424/1.65, 1.69, 9.1, 9.3, 9.4, 9.5, 9.6, 9.7, 424/9.8; 534/7, 10–16
See application file for complete search history.

(56) References Cited

U.S. PATENT DOCUMENTS
2007/0196331 A1 * 8/2007 Phillips et al. .......... 424/85.1

OTHER PUBLICATIONS

Kiuchi et al (Nippon Acta Radiological, 1994, vol. 54, pp. 1018-1029).*

* cited by examiner

*Primary Examiner* — D L Jones (57) ABSTRACT

The invention discloses one glyco-molecular imaging method for grade classification of liver fibrosis and its glyco-molecular imaging agent. The agent combining with glyco-molecular imaging method for liver targeting could be used to differentiate the grade of liver fibrosis and follow-up evaluation of the therapeutic effect.

4 Claims, 9 Drawing Sheets

GLYCO-MOLECULAR IMAGING METHOD FOR GRADE CLASSIFICATION OF LIVER FIBROSIS AND ITS GLYCO-MOLECULAR IMAGING AGENT THEREOF

FIELD OF THE INVENTION

The present invention relates to a molecular imaging method for quantification of liver fibrosis grade and its glyco-imaging agent with liver-targeting characteristics, wherein the agent combining with molecular imaging method could be used to differentiate the grade of liver fibrosis.

BACKGROUND OF THE INVENTION

In clinics, the liver fibrosis staging often depends on liver biopsy and Metavir classification which is classified F0, F1, F2, F3 and F4 according to the biopsy observation under microscopy. The biggest challenge for this method was its abhorrence by people for its latent danger. Besides, it is not accurate due to the frequent sampling error and deviation of individual observation. Furthermore, the result is qualitative and subjective but not quantitative and objective.

It has been well documented by Lee laboratory since 1983 that multivalent galactopeptide has a strong "cluster effect" to enhance binding with hepatic Gal/GalNAc receptor. The Gal-terminated triantennary structure exhibits $10^6$ fold stronger affinities than monovalent component structure. After binding, the galactopeptide will be endocytosis into hepatic cell. In 2004, Kwon's experiment indicates that the ischemic hepatic membrane has much lower Gal/GalNAc receptor and meanwhile, the endocytosis is also much less than the normal liver cell.

This invention discloses a molecular imaging method for quantification of liver fibrosis grade and its glyco-imaging agent with liver-targeting characteristics. This liver targeting glyco-molecular imaging provides the exact image distribution and real hepatic cellular uptake value, which objectivity overcomes the numerous uncertainty of present method.

SUMMARY OF THE INVENTION

It is therefore an object of the present invention to provide a molecular imaging method for quantification of liver fibrosis grades. There is no necessity to proceed the liver biopsy or body fluid sampling, which contains iv injection of galactopeptide imaging agent and read the total image signal per volume unit of liver within specified hours.

It is therefore another object of the present invention to supply a glyco-molecular imaging for accurate quantification of the liver fibrosis grades, which is made by a bifunctional chelator both linking to galactopeptide and chelating with a metal. Particularly, this bifunctional chelator has highly superior air stability than other bifunctional chelator. The storage time in room temperature is more than one year.

BRIEF DESCRIPTION OF THE DRAWINGS

The drawings, incorporated into and form a part of the disclosure, illustrate the embodiments and method related to this invention and will assist in explaining the detail of the invention.

DESCRIPTION OF THE PREFERRED EMBODIMENT

Figure 1:
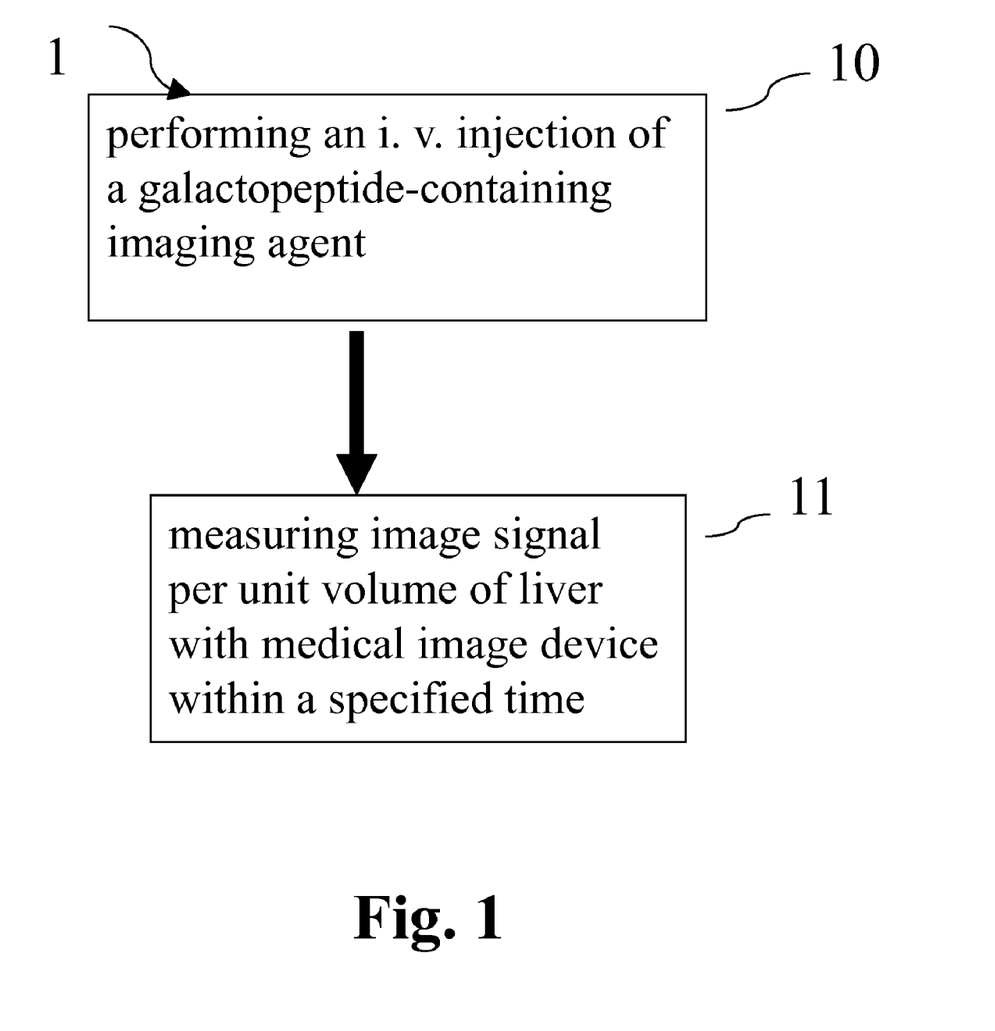
FIG. 1 is a graph showing clinical examination steps for differentiating liver fibrosis grades.

According to FIG. 1, method 1 was executed by a glyco-molecular imaging technique for liver targeting. There is no necessity to do any invasive tissue biopsy or body fluids sampling. The clinical examination steps including step 10 and step 11. In step 10, people were i.v. injected by galactopeptide molecular imaging agent and then the total imaging signal per volume unit of liver was measured by medical imaging device in the step 11. In which, the imaging agent could be radiopharmaceutical or magnetic contrast medium. One example shows Tc-99m-SOCTA-galactopeptide or Tc-99m-DTPA-galactopeptide combining SPECT (single positron emission computed tomography) for total γ emission count per unit volume of liver. Another example shows magnetic contrast medium, such as Mn-DTPA-glactopeptide or Gd-DTPA-galactopeptide, combining MRI (magnetic resonance imaging) for total magnetic resonance signal per unit volume of liver. In steps 11, the measurement time is below 6 hours.

Figure 3:
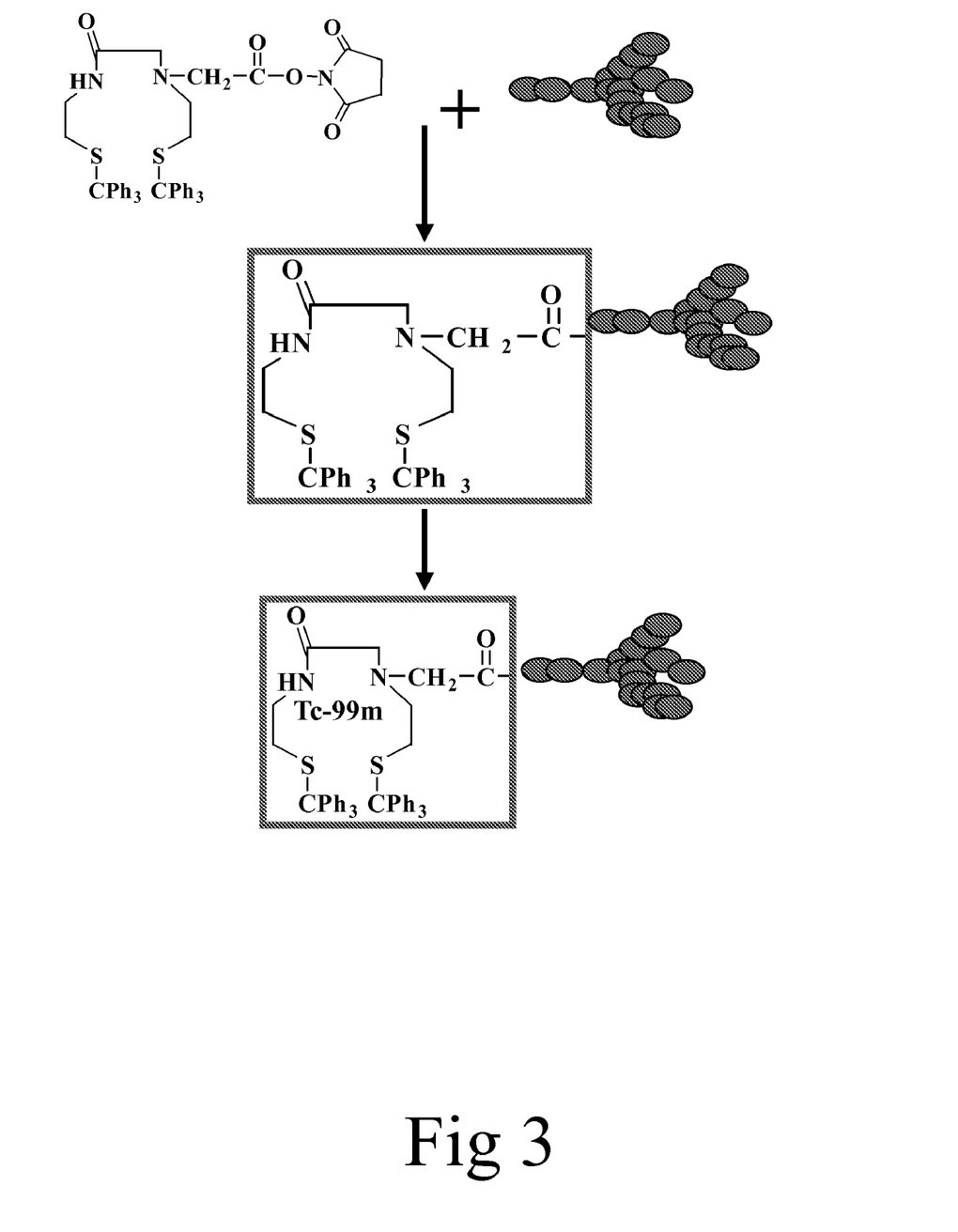
FIG. 3 is a graph showing the flow chart of preparation of Tc-99m-SOCTA-galactopeptide.

The present invention relates to the clinical usage of galactopeptide imaging agent, such as Tc-99m-SOCTA-galactopeptide, for liver fibrosis diagnosis. The rationale is that the collagen hyperplasia in liver fibrosis will bring the ischemia phenomenon in fibrotic liver. The more collagen produced, the more ischemia existed. Since we know the ischemia will reduce the uptake of imaging agent in liver, we believe Tc-99m-SOCTA-galactopeptide in FIG. 3 combining glyco-molecular imaging for liver targeting could be used for differentiating the fibrotic liver's grade. The molecular imaging is a prior art, so we do not describe the detail here. In FIG. 3, SOCTA means (succinimidyl-3,6-diaza-5-oxo-3-[2-((triphenyl-methyl)thio)ethyl]-8-[(triphenylmethyl)-thio]octanoate) and the structure thereof can be referred to in FIG. 4.

Figure 2:
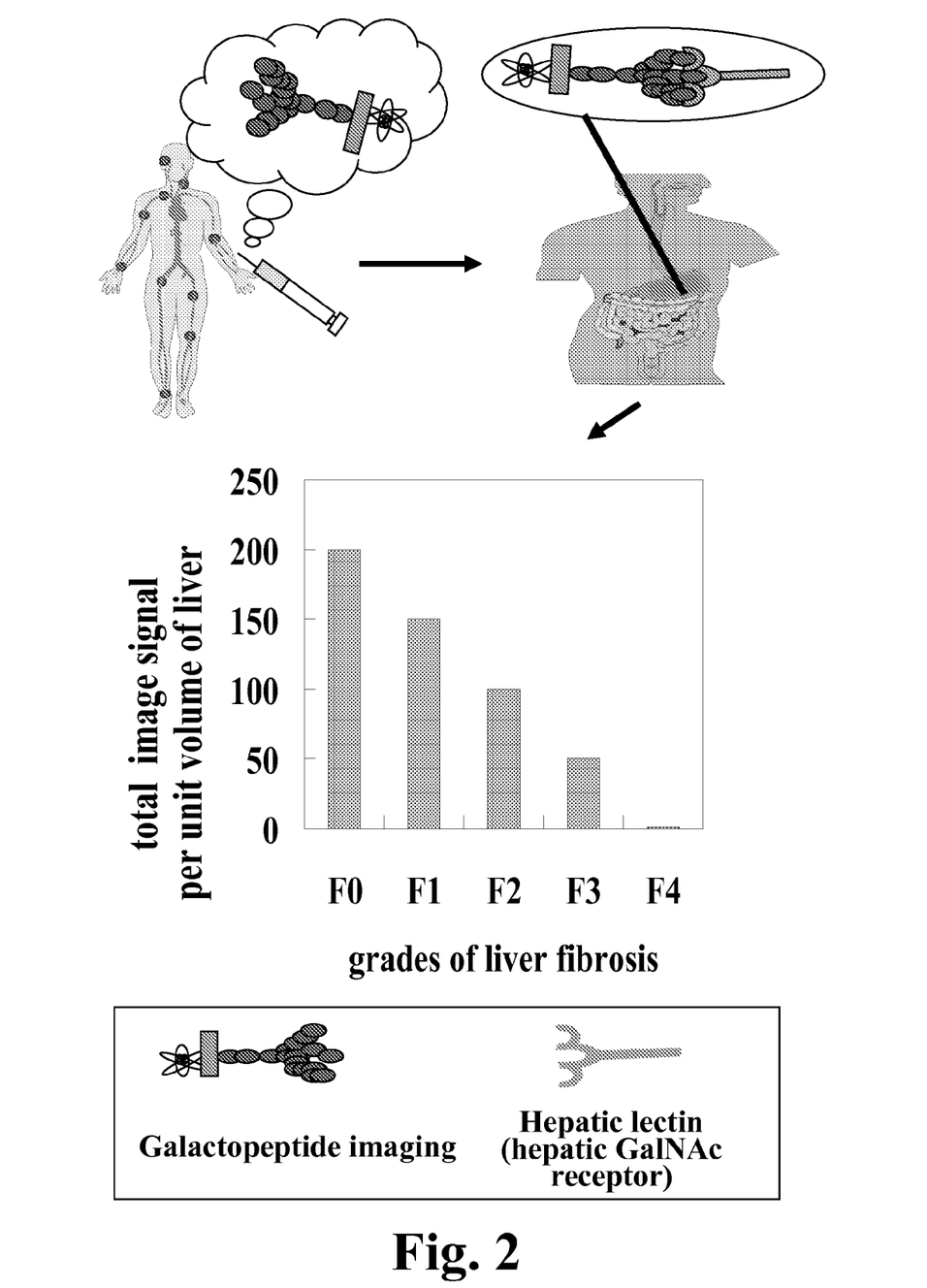
FIG. 2 is a graph showing the concept of glyco-molecular imaging for liver targeting.

FIG. 2 is the graph showing the concept of glyco-molecular imaging for liver targeting. There is no necessity of any liver biopsy or body fluid's sampling. If Tc-99m-SOCTA-galactopeptide or Tc-99m-DTPA-galactopeptide was used as the imaging agent, they will target to liver receptor and enter into liver cell by endocytosis after i.v. injected, combining the SPECT (single positron emission computed tomography), the emitted γ ray and liver volume will be measured, then the γ count per unit volume will be measured for liver fibrosis classification. If magnetic contrast medium, such as Mn-DTPA-galactopeptide or Gd-DTPA-galactopeptide, was used as the imaging agent, they will target to liver receptor and enter into liver cell by endocytosis after i.v. injected, combining MRI (magnetic resonance imaging), then the emitted magnetic resonance signal per unit volume of liver will be measured for liver fibrosis classification.

FIG. 3 is the preparation flow chart of Tc-99m-SOCTA-galactopetide. The preparation is fulfilled by conjugation of SOCTA with galactopeptide and then labeling with Tc-99m. The conjugation occurs by amino group of galactopeptide reacting with imidazole ester bond of SOCTA. The Tc-99m labeling occurs by linking with $N_2S_2$ structure of SOCTA. SOCTA could store at room temperature at last for one year due to its difficulty of water dissolution.

Theoretically, liver fibrosis will cause collagen hyperplasia from the surrounding of portal vein to the surrounding of central vein gradually, so that the blood flow into liver cell will expectedly reduced. That's why we propose the liver will be under ischemia status. The more collagen becomes hyperplasia, the more severity of ischemia. Since we know "the ischemic hepatic membrane has much lower Gal/GalNAc receptor and meanwhile, the endocytosis is also much less than the normal liver cell." from the prior art, we propose the fibrotic hepatic membrane has much lower Gal/GalNAc receptor, so that the endocytosis of Tc-99m-SOCTA-galactopetide will much reduced. That's why we reasonably derive Tc-99m-SOCTA-galactopeptide combining with the concept of glyco-molecular imaging for liver targeting could be used for liver fibrotic classification.

Figure 5:
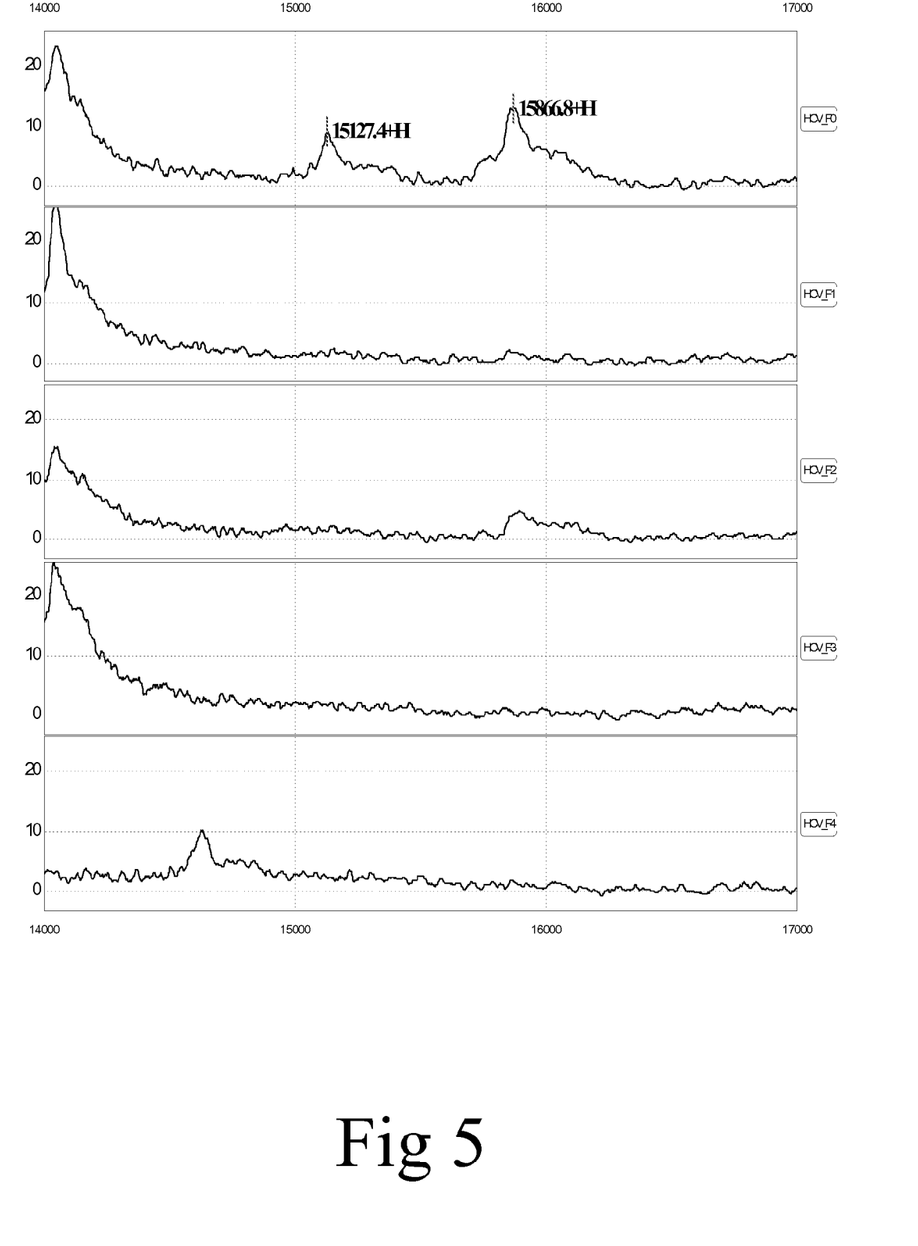
FIG. 5 is a graph showing mass spectrum of serum biomarkers with SELDI-TOF analysis.
Figure 6:
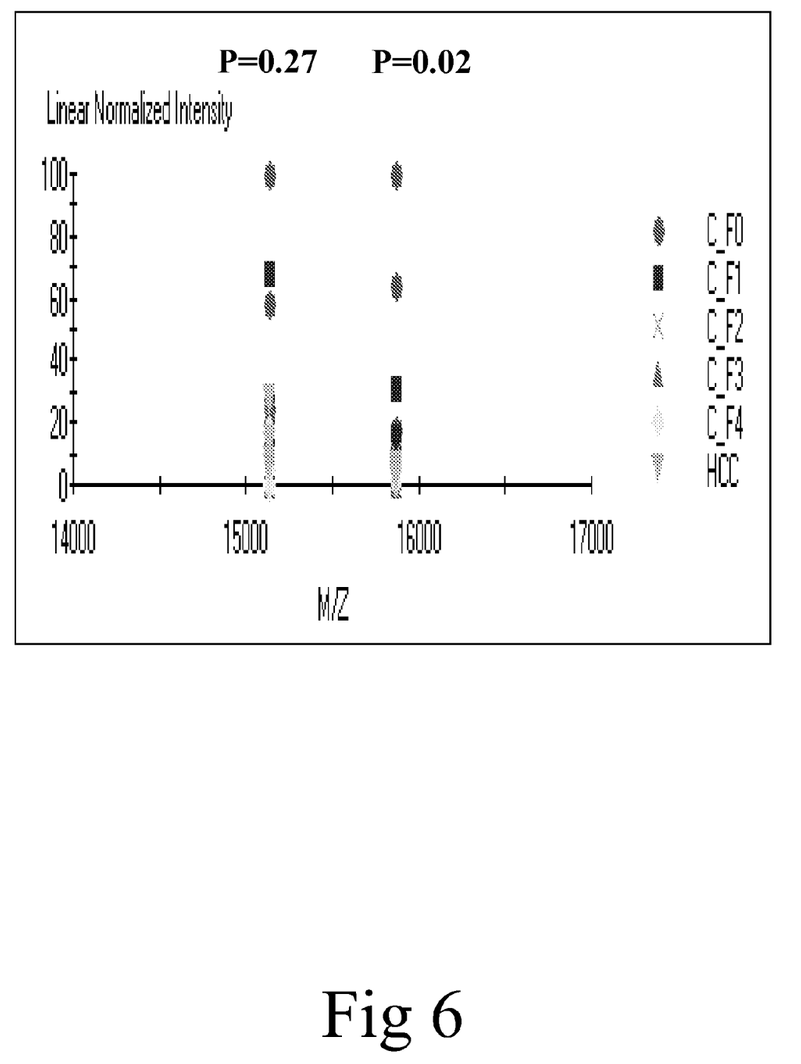
FIG. 6 is a graph showing statistics of serum biomarkers with SELDI-TOF analysis.

Experimentally, hemoglobin α chain (Molecular weight 15.1 kD) and hemoglobin β chain (molecular weight 15.9 kD) will reduced under ischemia status. We observe the change of these two protein peaks in serum with SELDI-TOF mass spectrometry. The results indicate the 15.1 kD and 15.9 kD exactly largely reduced in fibrotic liver. Please see FIG. 5 and FIG. 6. In FIG. 5, the Fo grade of fibrotic liver has higher concentration of these two protein peaks. By statistically analysis of these two protein peaks for 40 liver fibrosis patients in FIG. 6, the Fo grade of fibrotic liver has significant difference and higher concentration in 15.9 kD ($p=0.02$) and 15.1 kD ($p=0.27$).

Figure 7:
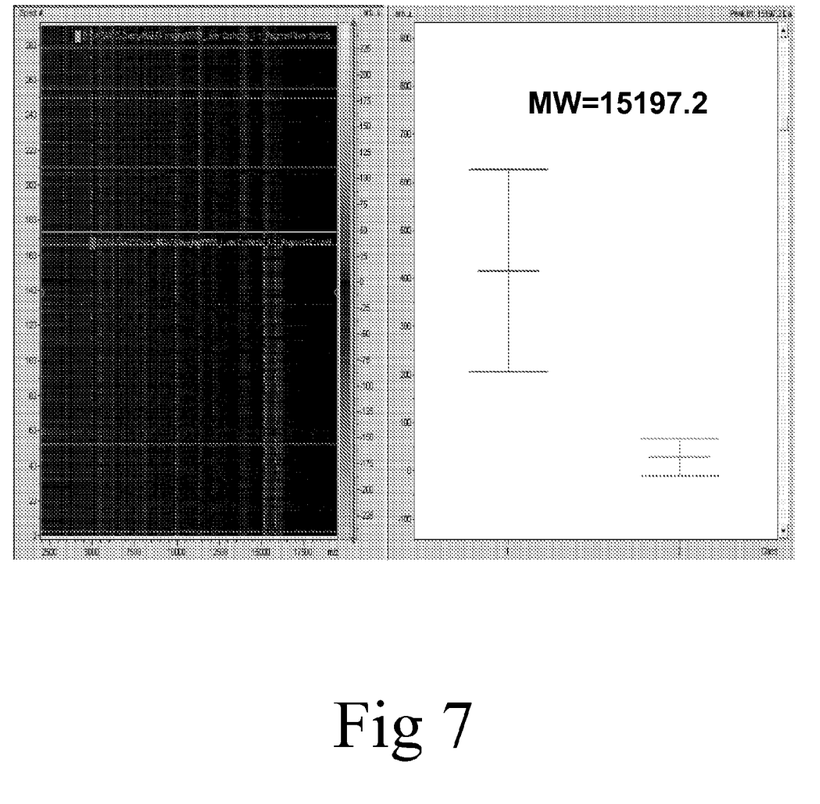
FIG. 7 is a graph showing the differential expression of 15.1 kD molecular weight protein in normal rat liver and fibrotic rat liver.
Figure 8:
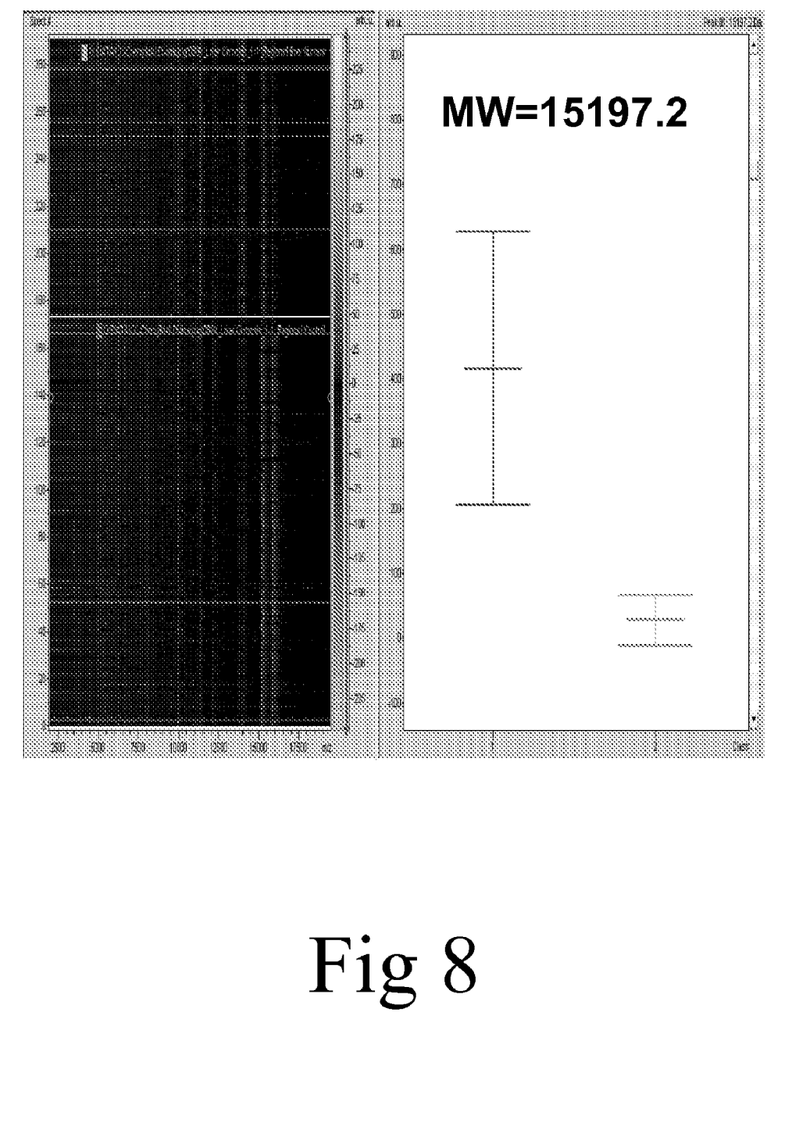
FIG. 8 is a graph showing the differential expression of 15.9 kD molecular weight protein in normal rat liver and fibrotic rat liver.
Figure 9:
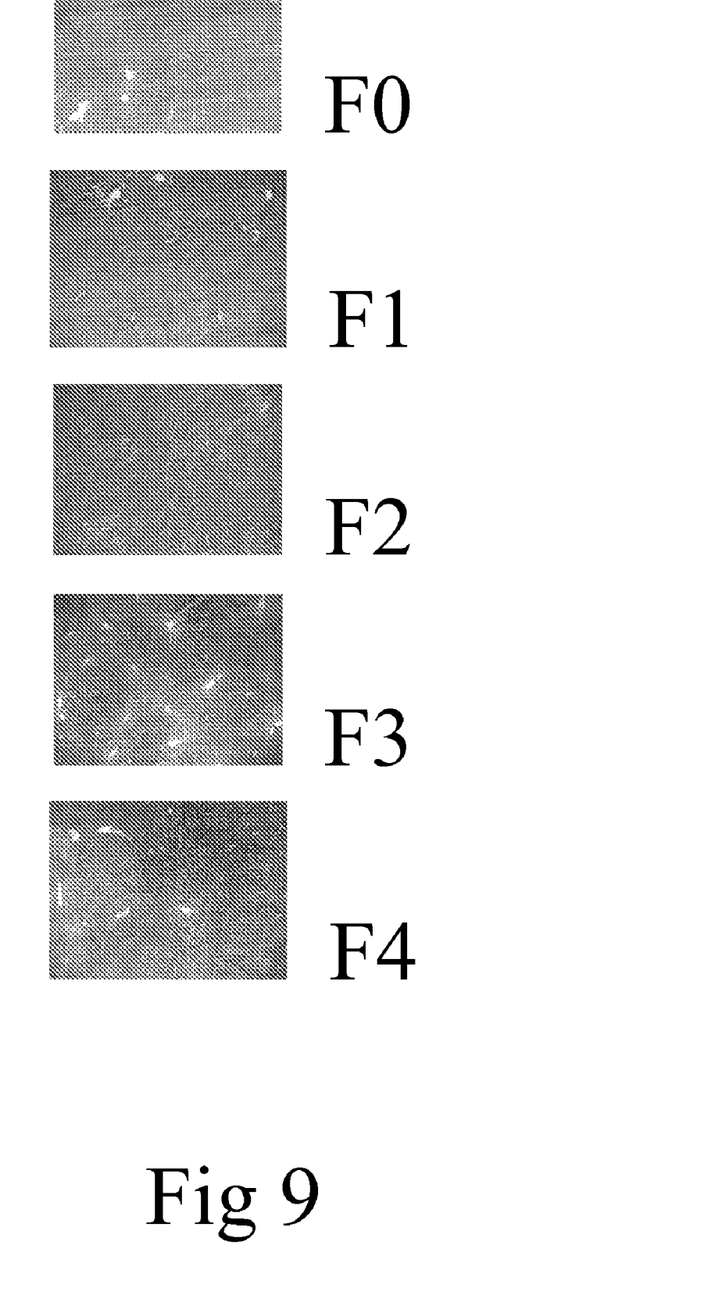
FIG. 9 is a graph showing the present grading result of fibrotic liver by pathological examination.

Similar results were shown in tissue profiling. In FIGS. 7 and 8, sections of 12 μm thickness were obtained on a cryostat at −18° C. and deposited on indium tin oxide coated conductive glass slides. Tissue sections were fixed by immersion in ethanol baths and allowed to dry for 30 min under vacuum. Matrix (for energy absorbed in mass spectrometry) deposition onto the tissue section was performed sequentially with 20 mg/mL sinapinic acid dissolved in 50% acetonitrile, 0.1% trifluoroacetic acid. MALDI MS spectra of the spotted tissue sections were acquired on an UltraFlex MALDI-TOF/TOF instrument. Either FIG. 7 or FIG. 8 supports fibrotic liver rat was under ischemia status. FIG. 7 shows fibrotic liver rat has much less protein expression at 15197.2 Da. FIG. 8 shows fibrotic liver rat has much less protein expression at 15858.3 Da.

Both hemoglobin α chain and β chain reduced in serum and tissue indicate fibrotic liver was under ischemia status. Glyco-molecular imaging for liver targeting provides image distribution data and quantification data. So that if they could be properly labelled with radioisotope or magnetic contrast medium and i.v. injection into body, they will be able used for grade classification of liver fibrosis and follow-up evaluation of the therapeutic effect.

Liver fibrosis could be totally recovered or improved if early diagnosis of liver fibrosis and proper therapy. Since the advantage of image distribution and quantification that glyco-molecular imaging for liver targeting could provide, it is beneficial to accurate fibrotic liver classification.

As to molecular imaging agent, we especially propose Tc-99m-SOCTA-galactopeptide used as quantification and differentiation of liver fibrosis. Galactopeptide has strong affinity with hepatic GalNAc receptor. A chelator such as SOCTA was essential for linkage between galactopeptide and Tc-99m. Traditionally, DTPA anhydride (DTPA: diethyl-triamine-penta-acetic acid) was used usually. DTPA anhydride reacts pretty quickly (often less than 2 hours) with amino group of galactopeptide in weak alkaline solution, meanwhile, it is not easy for storage in room temperature because it is much unstable and easy to water dissolution. Relatively, SOCTA is much stable and could store at room temperature lasting for one year. It reacts with galactopeptide much slowly, but it is much stable due to its difficulty for water dissolution. It is an advantage to be ingredients of image agent in a pharmacy plant due to its longer shelf life.

Figure 4:
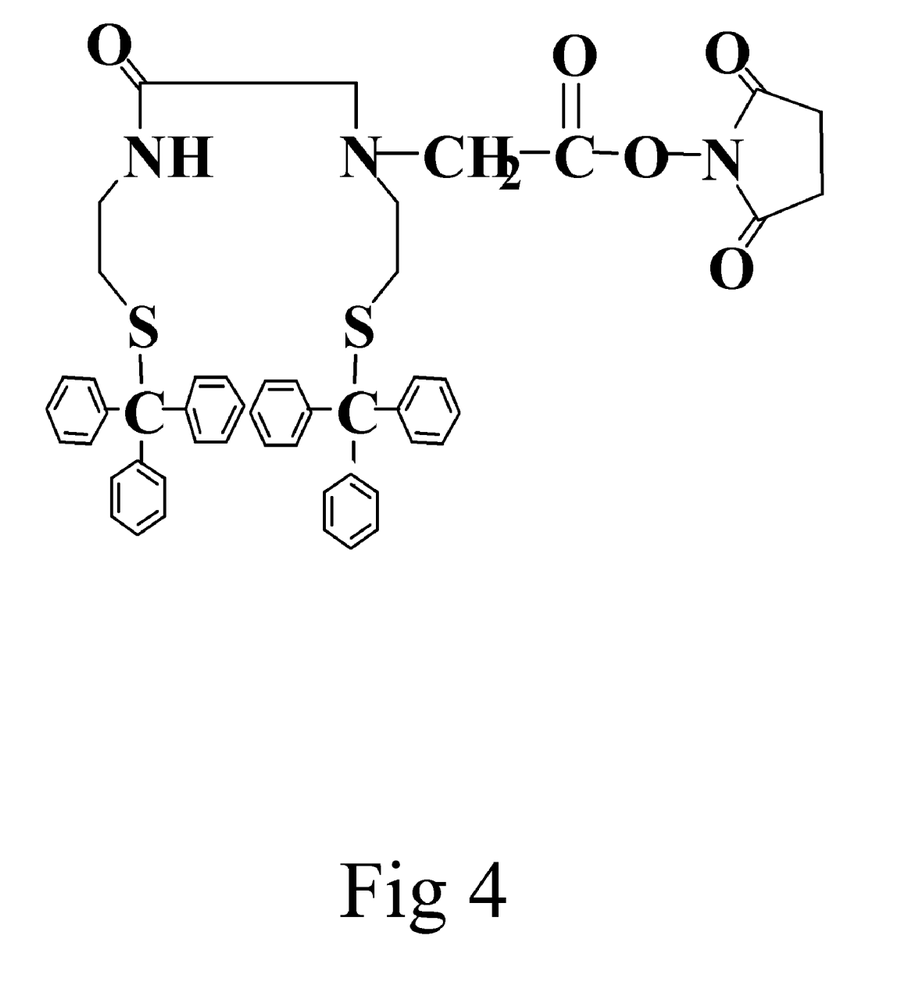
FIG. 4 is a graph showing the structure of SOCTA.

FIG. 4 is the chemical structure of SOCTA. The imidazole ester bond of SOCTA has the potential to conjugate with the amino group of galactopeptide and the $N_2S_2$ structure of SOCTA makes it be a good choice for Tc-99m labeling.

Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A method for accurate grade classification of liver fibrosis performed by glyco-molecular imaging for liver targeting without any necessity for tissue biopsy or body fluid sampling, comprising the steps of:
   (a) administering an intravenous injection of a galactopeptide-containing imaging agent wherein the imaging agent comprises a galactopeptide, a chelator, and a metal; and
   (b) imaging to measure total gamma signal per unit volume of liver with a SPECT or MRI scanner within a specified time;
   said galactopeptide-containing imaging agent is Tc-99m-SOCTA-galactopeptide.

2. The method of claim 1, wherein the specified time is less than 6 hours.

3. A glyco-molecular imaging agent for grade classification of liver fibrosis comprising a galactopeptide, a bifunctional chelator, and a metal;
   wherein the imaging agent is synthesized by conjugating the bifunctional chelator to the metal to form a bifunctional chelator metal complex; and
   said bifunctional metal chelator complex is linked to the amino group of the galactopeptide through an imidazole ester bond of said bifunctional chelator;
   said glycol-molecular imaging agent is Tc-99m-SOCTA-galactopeptide.

4. The agent of claim 3, wherein the galactopeptide is trivalent galactose.

* * * * *